United States Patent
Bush

(10) Patent No.: US 11,090,503 B2
(45) Date of Patent: Aug. 17, 2021

(54) NUCLEAR QUADRUPOLE APPLICATIONS FOR ENHANCED NERVE ION FUNCTION

(71) Applicant: Gary L. Bush, Riverhead, NY (US)

(72) Inventor: Gary L. Bush, Riverhead, NY (US)

( * ) Notice: Subject to any disclaimer, the term of this patent is extended or adjusted under 35 U.S.C. 154(b) by 320 days.

(21) Appl. No.: 16/383,637

(22) Filed: Apr. 14, 2019

(65) Prior Publication Data

US 2020/0324134 A1 Oct. 15, 2020

(51) Int. Cl.
*A61N 2/00* (2006.01)
*A61N 1/40* (2006.01)

(52) U.S. Cl.
CPC .............. *A61N 2/006* (2013.01); *A61N 1/40* (2013.01); *A61N 2/008* (2013.01)

(58) Field of Classification Search
CPC ...... A61N 1/40; A61N 2/008; A61N 1/36031; A61N 2/006
See application file for complete search history.

(56) References Cited

U.S. PATENT DOCUMENTS

| | | | |
|---|---|---|---|
| 5,497,773 A * | 3/1996 | Kuhara | G01R 33/56554 324/318 |
| 5,899,922 A | 5/1999 | Loos | |
| 6,344,818 B1 | 2/2002 | Markov | |
| 7,151,914 B2 | 12/2006 | Brewer | |
| 7,341,446 B2 | 3/2008 | Bush | |
| 8,457,757 B2 | 6/2013 | Cauller et al. | |
| 9,144,682 B2 | 9/2015 | Starobin et al. | |
| 9,358,374 B2 | 6/2016 | Dacey, Jr. et al. | |
| 9,713,720 B2 | 7/2017 | Zhu | |
| 9,717,921 B2 | 8/2017 | Perryman et al. | |
| 9,744,347 B2 | 8/2017 | Chen et al. | |
| 10,048,347 B2 | 8/2018 | Kudielka et al. | |
| 10,088,540 B2 | 10/2018 | Song et al. | |
| 2008/0046037 A1 | 2/2008 | Haubrich et al. | |
| 2016/0287887 A1 | 10/2016 | Wu et al. | |

(Continued)

OTHER PUBLICATIONS

Bazaka, Kateryna, et al., "Implantable Devices: Issues and Challenges", Electronics, v. 2, pp. 1-34 (2013).

(Continued)

*Primary Examiner* — Christine H Matthews
*Assistant Examiner* — Joshua Daryl D Lannu
(74) *Attorney, Agent, or Firm* — Jack V. Musgrove

(57) ABSTRACT

A method of enhancing nerve function by directly stimulating the atoms transgressing the architecture of an ion channel utilizing one or more nuclear quadrupole resonant frequency stimuli targeted at the specific ions in their particular environment. By altering the spin state of the atoms, Na+ and K+ for example, they may more readily navigate the natural barriers necessary for both the rapid throughput and high selectivity that are characteristic of ion channels. The method and applications are primarily directed at inadequate nerve function resulting from injury or disease; however, a direct opposite approach may be used to block nerve responses for the purpose of pain management. The system includes feedback control of four signal parameters: frequency, interval, width and amplitude. The method may utilize multiple resonant stimulators, including implanted devices which can communicate with one another.

23 Claims, 5 Drawing Sheets

(56) References Cited

U.S. PATENT DOCUMENTS

2017/0143969 A1* 5/2017 Sarpeshkar .......... A61N 1/0551

OTHER PUBLICATIONS

Chow, "Implantable RF Medical Devices: The Benefits of High-Speed Communication and Much Greater Communication Distances in Biomedical Applications", IEEE Microwave Magazine, v. 14, n. 4, pp. 64-73 (2013).
Ferguson, John, et al., "Wireless communication with implanted medical devices using the conductive properties of the body", Expert Review of Medical Devices, v. 8, n. 4, pp. 427-433 (2011).
Kratochvil, Huong, et al., "Instantaneous ion configurations in the K+ ion channel selectivity filter revealed by 2D IR spectroscopy", Science, v. 353, n. 6303, pp. 1040-1044 (2016).
Roux, Benoit, "Ion channels and ion selectivity", Essays in Biochemistry, v. 61, n. 2, pp. 201-209 (2017).
Rutkove, Seward, "Electrical Impedance Myography: Background, Current State, and Future Directions", Muscle Nerve, v. 40, n. 6, pp. 936-946 (2009).
Sagan, Didier, "RF Integrated Circuits for Medical Applications", Zarlink Semiconductor Ultra-Low Power Communications Division, San Diego, California (2005).
Sansom, Mark, et al., "Potassium channels: structures, models, simulations", Biochimica et Biophysica Acta—Biomembranes, v. 1565, n. 2, pp. 294-307 (2002).
Tyler, William, et al., "Remote Excitation of Neuronal Circuits Using Low-Intensity, Low-Frequency Ultrasound", PLoS ONE, v. 3, n. 10 (2008).

* cited by examiner

NUCLEAR QUADRUPOLE APPLICATIONS FOR ENHANCED NERVE ION FUNCTION

BACKGROUND OF THE INVENTION

Field of the Invention

The present invention generally relates to medical applications for nerve function, and more particularly to a method of enhancing conduction through nerve ion channels.

Description of the Related Art

The human nervous system is likely the most enigmatic feature of the human body. It is important not only for controlling muscle movement and response, but also for detecting sensations, particularly pain. There are many prior art systems that relate to stimulating nerves in order to achieve various medical goals such as pain management. U.S. Pat. No. 5,899,922 is directed to the manipulation of nervous systems by electric fields. U.S. Pat. No. 9,144,682 illustrates the stimulation of nerve tissue with a sequence of spatially-distributed resonant sub-threshold electrical stimuli to restore nerve conductivity. U.S. Pat. No. 9,358,374 relates to blocking nerve conduction with various blocking stimulus sources such as electrical, magnetic, ultrasonic, optical, thermal, or chemical. U.S. Pat. No. 9,713,720 describes a neurostimulation system with three-dimensional lead migration detection and automatic neurostimulation correction. U.S. Pat. No. 9,717,921 shows the treatment of inflammation, chronic pain and other disorders with neuromodulation. U.S. Patent Application Publication No. 2017/0143969 discloses multi-electrode, energy-recycling, resonant stimulation circuits and architectures for nerve blocking. U.S. Pat. No. 5,497,773 discloses a method of protection against nerve stimulation for patients undergoing magnetic resonance imaging.

None of these systems discuss nerve ion channels or ion conduction. Ion channels are one of the most complex and researched areas in all of science. A major advancement toward the understanding of ion channel function occurred roughly twenty years ago when the structure of the potassium ion (K+) channel was more precisely mapped by use of 3D x-ray crystallography. This discovery increased knowledge of a more exact model of the ion channel, greatly expanded and confirmed the "snug fit" explanation of ion function described throughout the mid to late $20^{th}$ century research, and stimulated additional research in other theoretical explanations involving throughput and selectivity. The article "Potassium channels: structures, models, simulations" by Mark Sansom et al. is an example of observations of ion function after the introduction of 3D x-ray crystallography.

Two additional theories of ion function emerged in the years following the enhanced imaging 3D x-ray crystallography breakthrough. One area of ongoing interest involves thermodynamic dehydration energy differences between different ions. Another subset approach focuses on Coulomb energy interactions, or "knock on" theory, between ions in the selectivity filter of the channel. Both theories serve to further explain why ion channels have very high throughput while maintaining a high degree of selectivity. Recent approaches (Roux, "Ion channels and ion selectivity", 2017; Kratochvil et al., "Instantaneous ion configurations in the K+ ion channel selectivity filter revealed by 2D IR spectroscopy", 2016) utilize computational molecular dynamics and 2D infrared spectroscopy respectively to provide additional insights into both theories. K+ channels have been much more researched in the past than Na+ (sodium ion) channels. Recent results of research into Na+ channels reveal some general similarities to K+ albeit a much larger diameter of the selectivity filter. Consequently, it is believed that sodium ions may pass through the Na+ channel selectivity filter while hydrated. This is a major difference as K+ navigates the filter while dehydrated. The role of nerve ion conduction for medical applications is heretofore unknown.

SUMMARY OF THE INVENTION

The present invention in at least one embodiment is generally directed to a method of enhancing nerve ion function in a human by stimulating one or more selected nerve ions using nuclear resonance to alter an ion channel conductivity of the one or more selected nerve ions wherein the nuclear resonance stimulation has one or more signal parameters including a frequency targeted for the one or more selected nerve ions, iteratively sensing one or more indicia of nerve function, and automatically adjusting one or more signal parameters of the nuclear resonance stimulation in real-time based on the sensed indicia. The stimulating preferably utilizes nuclear quadrupole resonance. The adjusting can selectively increase or decrease the frequency of the nuclear resonance stimulation by a predefined frequency adjustment value. The signal parameters can further include an interval, a width, and an amplitude, and the adjusting can allow independent adjustment of each of these signal parameters. The indicia can indicate a current improvement in nerve function whereupon the adjusting responsively increases a magnitude of the one or more signal parameters. In one implementation the selected nerve ion is a potassium ion, and the stimulating emits an electromagnetic signal having a frequency which targets a nuclear resonance frequency of the potassium ion. Additionally, the one or more selected nerve ions could include a first ion isotope and a second ion isotope wherein the nuclear resonance stimulation frequency is a first frequency targeted for the first ion isotope, and the stimulating can further simultaneously use nuclear resonance stimulation having a second frequency targeted for the second ion isotope.

The above as well as additional objectives, features, and advantages in the various embodiments of the present invention will become apparent in the following detailed written description.

BRIEF DESCRIPTION OF THE DRAWINGS

The present invention may be better understood, and its numerous objects, features, and advantages of its various embodiments made apparent to those skilled in the art by referencing the accompanying drawings.

The use of the same reference symbols in different drawings indicates similar or identical items.

DESCRIPTION OF THE PREFERRED EMBODIMENT(S)

Figure 1:
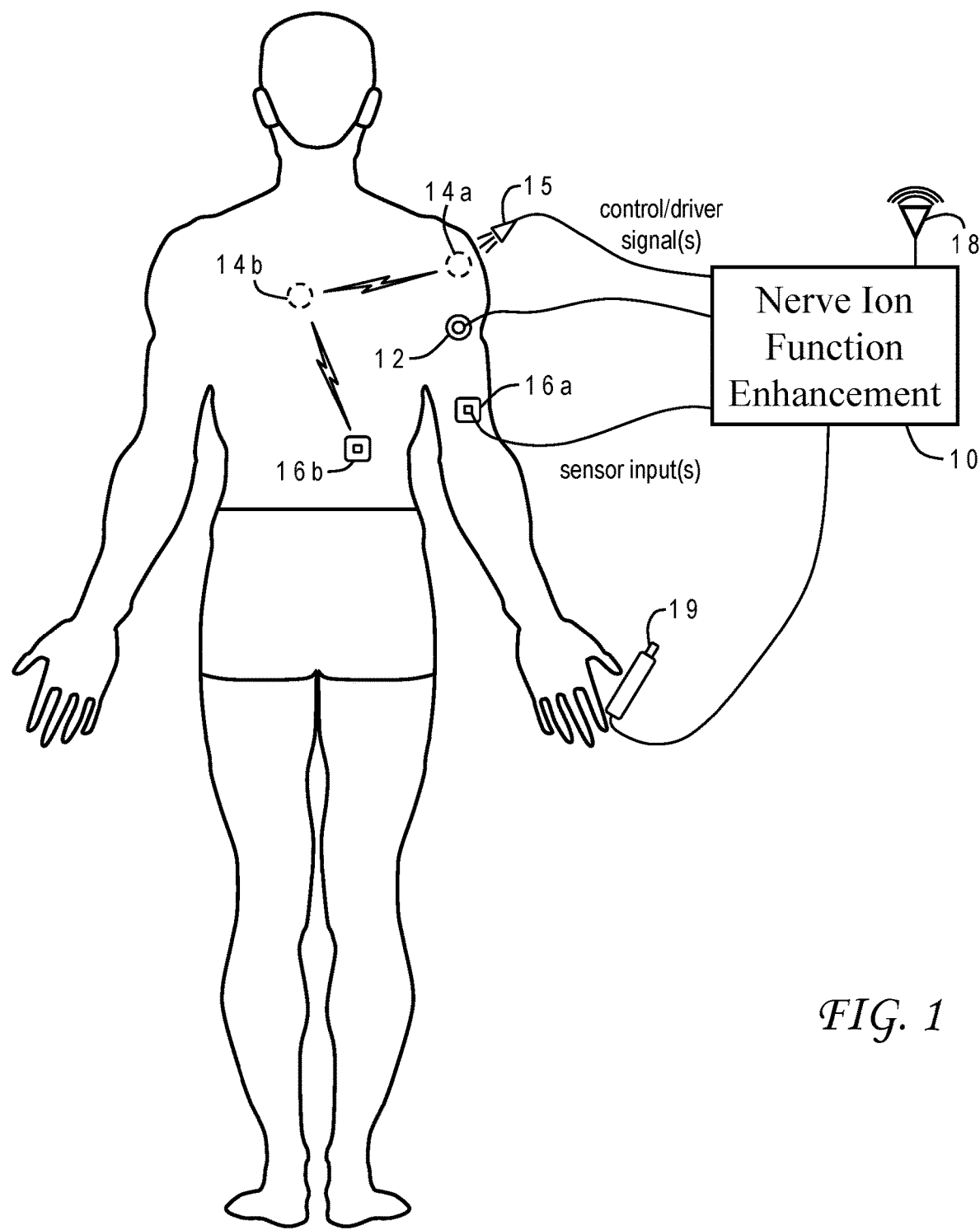
FIG. 1 is a pictorial representation of a human undergoing therapy using a nerve ion function enhancement apparatus in accordance with one implementation of the present invention.

Voltage-gated ion channels include K, Na, Ca, and Cl. There are expected significant differences in the function and architecture of each. Within each are subsets which will also have unique differences. For example, there will be expected differences between both an individual K+ and Na+ channel in different species. It would be beneficial to first to attempt to understand the function of the most researched and studied K+ channel, develop applications to enhance function for variables such as damage or disease, and then utilize similar techniques where overlap occurs in other ion types. It is expected that same species Na+ and K+ channels will perhaps have more similarities than almost all other possible comparisons.

Ion channels rapidly open and close (polarize and depolarize) to initiate a voltage differential, or action potential, in a neuron. This voltage pulse travels at approximately 120 m/sec along the nerve to stimulate the intended response.

A broad, very general, physical description if an ion channel is by way of a comparison to an hour glass. The exterior and interior pores of the cell can be visualized as well as the narrowest portion of the hour glass which equates to the ion channel selectivity filter. Although the entire ion channel structure in some way contributes to ion passage, the architecture of the filter is key to understanding both selectivity and throughput.

The selectivity filter is surrounded by protein structures. Of particular interest, are portions of eight protruding oxygen atoms which make up part of the backbone carbonyl molecules of the protein structure surrounding the filter. These paired semi-rigid oxygen atoms are centrally aligned 90 degrees apart in the (for example) 3-6-9-12 positions of a clock. Their purpose is to restrict passage of ions that cannot align their single outer electron orbit orientation to allow both high selectivity and rapid throughput.

Further examination of the physical structure of the channel is necessary for further clarification.

Among the unknowns is how the ion channel can be so selective while allowing such rapid throughput. Research in the past two decades very accurately mapped the architecture of nerve ion channels, in particular the KcsA+ channel (a prokaryotic potassium channel from soil bacteria), which opened many doors for further research. Nevertheless, a significant number of questions remain unanswered.

The research of the structure of the different channels has revealed that there are similarities between mutations but that each specific ion channel is unique for each specific ion. For simplicity, the method and applications described are directed at K+, while suggesting similarities most likely exist with Na+ channels.

The K+ voltage gated channel is more researched and therefore more understood than different mutations. Inside the channels are four stages of selectivity barriers or binding sites, commonly referred to S-1, S-2, S-3, and S-4. In K channels, dehydrated K+ ions enter at the intracellular side (S-4) single file and exit at the extracellular mouth of the channel at a site sometimes referenced as S-0. Eight protruding oxygen atoms at each binding site, which are part of the carbonyl atoms of the surrounding protein structure, form a very defined (but somewhat flexible) restriction barrier at binding sites S-1 through S-4 through whereby only specific ions, with very few exceptions, can pass. The restriction geometry is such that the eight oxygens are grouped into four pairs. The simplest description of their arrangement is by comparison to the 2D face of a clock. The four pairs would be centered at the 3,6, 9, and 12 o'clock positions. A single ion transgressing the channel passes through the center of the clock face in the 3D (Z) axis. Basically, from depicted research figures, the individual oxygens would be at approximately the 2:30, 3:30, 5:30, 6:30, etc. positions. It has not yet been determined if (but assumed true) that all binding sites are aligned in the identical configuration. For purposes of discussion, the pairs of oxygens are expected to be centered 90 degrees apart.

The single file transgressing K+ ion has very little room to maneuver inside the selectivity filter as the precise physical dimensions of the filter itself is structured to be of a diameter to accommodate similar sized desired ions. This is known as the "snug fit" explanation which contributes to overall selectivity. Each individual ion passing through the channel is almost always separated by a single water molecule. The purpose of this water molecule escort is, to date, unexplained.

The physical dimensions of the selectivity filter of the channel is about 3 Å wide and around 10-15 Å long. The throughput of K+ ions transgressing the channel is several million per second. More precise estimates in past research suggest a throughput range of about 1-100 million/sec. The time required for a single K+ ion to travel from S-4 to S—0 is 2.5 times the flowrate. For example, the time required at a throughput rate of 1 million/sec would be 2.5 microseconds.

The throughput of the filter/channel can vary somewhat depending on ion occupancy configuration in S0-S4 at any given time. For example, if a Na+ ion is by chance passing through the filter (estimated 1 Na+ per 1,000 K+), the width of the channel is thought to constrict slightly (speculated at 0.4 Å) at the binding sites to accommodate. This constriction would most likely limit throughput to the lower estimate (1 million/sec) of the range. A throughput closer to the higher rate would be expected when the channel functioning in the optimal state of single file K and water whereby occupancy of S-4 to S-0 would be either K-W-K-W-K or W-K-W-K-W. In addition, the larger Rb+ ion can occasionally pass through the filter.

Supporting the contributing "snug fit" explanation for selectivity are the atomic radii of the above mentioned atoms—K (1.31 Å), Na (0.95 Å), and Rb (1.48 Å). The estimated 0.4 Å deformation of the carbonyl oxygen protrusions at the binding sites is thought to be a result of the roughly same difference between the K and Na radii. The $H_2O$ molecule, although not involved in electrostatic forces within the filter, has a radius of 1.38 Å.

Na hydrated ions are normally depicted as having six symmetrically attached $H_2O$ molecules. Hydrated K is usually depicted as having six or sometimes four attached $H_2O$s while Rb is most often shown with four. As K+ ions enter the selectivity filter they are dehydrated.

$H_2O$ is a highly polar molecule and exhibits a stronger binding energy to smaller radii ions vs larger. It therefore requires more energy to dehydrate the smaller Na ion than K. Select dehydration energies (kcal/M) are Na-105, K-85, and Rb-79. Many believe that these thermodynamic dehydration differences are the primary reason for K selectivity over Na, because, in other words, it is the path of least resistance.

Others point to electrostatic attraction/repulsion forces, "knock on" approach, as a third likely explanation for both the channel's high selectivity and throughput. Supporting this theory are the recently discovered (via ultrafast time resolution IR spectroscopy and ever more sophisticated computational modeling) higher efficiencies depending on the neighboring occupancy variables at individual binding sites.

The well-researched "snug fit", "thermodynamic dehydration energy differentials", and "knock on" established theories all contribute to understanding ion channel efficiency (throughput and selectivity).

Many unknowns remain such as why there are four binding sites required and not one or three? Why are there four pairs of symmetrically positioned oxygen molecules and not two or eight? Why does a single water molecule almost always separate ions while they pass through the filter, what is its purpose, and how is it physically placed there? Examination of the specific nuclear forces influencing the channel may serve to further support established theory while additionally shedding some light on the many remaining unknowns, particularly, nuclear quadrupole resonance.

Nuclear quadrupole resonance (NQR) is a much more unexplored area of nuclear physics than nuclear magnetic resonance (NMR). A brief descriptive comparison of both sciences may further explain the very complex selectivity filter dynamics.

Nuclear resonance is a phenomenon associated with the protons or nuclei of an element. The nuclei of all elements carry a positive charge. When the spins of the protons comprising a nucleus are not paired, the overall spin of the charged nucleus generates a magnetic dipole along the spin axis. The intrinsic magnitude of this dipole is a fundamental nuclear property called the nuclear magnetic moment. Certain atoms and molecules can be excited by the application of an electromagnetic field which interacts with the magnetic dipoles formed by the nuclei. Not all nuclei possess spin (i.e., their spin number is 0), and those elements having no nuclear spin (and hence, no dipole moment) cannot be affected using nuclear resonance. Abundant elemental components of organic material that have spin numbers of 0, and therefore are not candidates for nuclear resonation, include C-12 and O-16.

Nuclear magnetic resonance (NMR) utilizes a static magnetic field and a second oscillating magnetic field to perturb the nuclei of material under inspection. The rotational axis of a spinning nucleus is not orientated exactly parallel (or anti-parallel) with the direction of the applied magnetic field, but rather precesses about this field at a known angle and with an angular velocity that depends upon the magnetic moment. A given set of distinct protons transitioning between quantum states will produce an electromagnetic (sine) wave whose frequency matches their precession frequency. The effective magnetic field around a given nucleus can also be affected by the orientation of neighboring nuclei, and may lead to spin-spin coupling which splits the signal for each type of nucleus into two or more spectral lines. The signal detected at the NMR receiver thus resembles a collection of exponentially decaying sine waves, and is referred to as a free induction decay (FID). Analysis of the FID yields frequencies associated with known chemical structures. Two-dimensional spectroscopy techniques are used to determine the structure of more complicated molecules. NMR has heretofore been used primarily for imaging purposes, such as in magnetic resonance imaging (MRI) for medical diagnostics.

Some nuclei possess electric quadrupole moments (non-spherical electric charge distributions). Nuclear quadrupole resonance (NQR) can be utilized on such substances. NQR is a branch of radio frequency spectroscopy that has been used quite effectively for the detection of contraband and other items of concern such as explosives. A radio frequency pulse generated by a transmitter coil causes the excitation of nuclear spins to higher quantum energy levels. When the nuclear spins return to their equilibrium position, they again follow a particular precession frequency based on their quadrupole moments. In NQR substance detection, a receiving coil is used to measure and analyze the energy released from the resonated nuclei as they return to their normal spin states. Measurement of this released energy (and/or relaxation time constants) can indicate not only which nuclei are present but also their chemical environment. The environmental variables of temperature, pressure, and molecular composition (as opposed to free-form or unbound atoms) will alter the resonant frequencies and spin relaxation times of otherwise identical isotopes of NMR/NQR receptive elements. U.S. Pat. No. 10,088,540 describes the use of more than one NQR stimuli simultaneously at different frequencies without interference.

Relaxation times are inherently much shorter in the science of NQR as opposed to NMR. Therefore, this disclosure is mostly directed to the placement of NQR components in various nerve ion channel enhancement systems. Exact relaxation times for different nerve enhancement techniques can vary considerably; however, for the techniques contemplated by the present invention, it is believed that they are approximately one microsecond for NQR targeted atoms when in free-form as compared to one millisecond for NQR atoms when found in a bound molecular environment.

The shapes of electron orbitals around the nuclei of single unbound atoms are most often described in science by use of areas of probability. These areas of higher probability are often described as the electron cloud. The shape of the electron cloud is influenced by both internal and external forces. Examples of internal forces are the degree of axis wobbling of the nucleus and repulsion forces of neighboring electrons occupying the same shell. The shape of an isolated single valence electron cloud (atoms with a single electron in their outer shell) are somewhat more predictable and defined than multiple electron occupied outer shells and are most often described as a tear drop shaped figure eight in a 2D plane.

The predicted electron cloud is only useful in describing unbound atoms separated from any external forces that may influence its motion. Examples of external forces are the proximity of surrounding atoms/molecules, transient magnetic fields, collision forces, tumbling of the nucleus, vibration, temperature, pressure, etc. Consequently, because of rapid motion and internal/external forces, the electron cloud of an unbound atom's outer shell can most simply be described as the surface of a sphere.

Input nuclear resonant stimuli frequencies are different for each specific atom. Examples of the environmental influences on targeted atoms include the strength of a static magnetic field, temperature, and pressure. Of these, the strength of the static magnetic field has the most direct influence. There exists a direct correlation between magnetic field strength and resonant frequencies as can be found in 3 T compared to 1.5 T MRI (NMR). The correlations between temperature, pressure, and frequency are not as direct.

From further analysis of the ion channel it is highly likely that the ions must be somewhat aligned to physically fit through and navigate the architecture. The valence electron in the K+ or Na+ also most likely cannot be tumbling to efficiently fit through the narrow angle of passage (<90 degrees) of the fixed carbonyl electrons.

It is established that an atom absorbs energy (RF, laser pulsed in the RF range, vibrational, or other) when resonated and in turn releases energy as it returns to its normal state. It is not established and unknown in science whether the electrons of an NMR or NQR stimulated nuclei briefly alter their orbital patterns. Supporting evidence suggests that they do. All forces of the protons in the nucleus are balanced or offset by its orbiting opposite charged electrons. For example, atoms with a nuclear spin number of 0 (e.g., carbon, oxygen, nitrogen) typically make up the strongest bonds in molecules whereas ½ spin (NMR) and >½ spin (NQR) do not. In fact, past experimental research has shown that very weak chemical bonds can sometimes be broken by resonating the NQR nuclei of some molecules.

The orbital deflection angle of the valence electrons of the ion transgressing the membrane must not necessarily be perfectly aligned for passage. It is, however, highly suggestive that they do require some degree of stability from their normal random orbital patterns in order to achieve highly efficient throughput rates.

Analysis of the dynamics involved in selectivity filter function can be further understood by considering the dehydration of a K+ ion approaching the S-4 binding site entry as, not only an electrostatic repulsion separation, but rather a collision. As the K atom approaches S-4, 4 of its 6 attached water molecules will be separated by the 4 protruding oxygen restrictions centered 90 degrees apart in the x- and y-axis (3, 6, 9, and 12 o'clock positions, e.g.) in the filter. These four electro-mechanical perpendicular shear force collision energies are different than those required for the remaining two water molecules. The water molecule attached at the 3 o'clock position in the z-axis, the most protruding into the filter at this point, is also separated due to the collision forces involved and becomes the escort molecule separating K+ ions during filter passage. The K+ atom's velocity is briefly, and minutely reduced, as compared to this single separating water molecule. The remaining water molecule (9 o'clock, z axis, outside during collision) is separated prior to S-4 passage, most likely by a collision rebound force, and does not enter the filter.

It can now be understood how a single water molecule is separated and "almost always" placed in between each single file K+ atom in the selectivity filter. The reason why there occasionally may not be a single water molecule separation could be explained when the K+ atom is sometimes hydrated by four attached water molecules instead of six.

As the hydrated K+ ion approaches S-4 and sheds its water molecules, the single orbiting electron in its outer shell electron will instantaneously reconfigure its energy to the path of least resistance. That path of least resistance will be an orbit angle midway between the repulsion forces of the oxygen protrusions (45 degree offset). In other words, the single electron orbital axis will be reoriented to either a 2:30/7:30 or a 10:30/4:30 axis in the x-y plane and with rotational direction in the z-axis. Very minimal resultant torque forces will occur on the filter structure during this electron reorientation. Due to the rigidity and high repulsive force of the paired oxygen obstacles, the electron cloud of the single K+ orbiting electron will shrink substantially from its natural unbound tear drop figure eight shape to one more closely resembling a straight line. As the electron orbitals shift to a more aligned and less random state, the nucleus will also restructure to a more regimented and less kinetic equilibrium.

Essentially, it is suggested, the selectivity filter structure electro-mechanically resonates the K+ ion as it enters and while it passes through the membrane. Remaining unanswered questions may provide contributing evidence on why this may be true. One example would be the purpose of the single separating water molecule.

The "knock on" theory has established that the K channel has the most efficient (100 million/sec) throughput when only K+ ions and water occupy the binding sites. The presence of a single Na or Rb atom, or the lack of a separating water molecule, all cause the efficiency and throughput rate to decline substantially to a slower 1 million/sec rate. At this slower rate, the resonated K atom will not pass entirely through the filter before it begins to return to its non-resonated relaxed state. In fact, because it requires 2.5 microseconds to pass from entry to exit during reduced flow rates, it may be resonated twice, first at S-4 and then again at or in the space between either S-2 or S-1. This realization may explain one reason why there are four binding sites and not one or eight. The four binding sites appears to be the optimal number for the tradeoff considerations of both selectivity and throughput efficiency.

When a resonated K+ ion returns to its relaxed state while still in the selectivity filter, it will emit energy in a decaying manner. This energy release would most likely, but not necessarily, be in the form of electromagnetic or vibrational energy. This may be some sort of signal to the surrounding protein structure to retune when the throughput rate is reduced due to Rb or Na or transgressing the filter. The purpose of the separating water molecule can now be speculated to be either a buffer or absorbent of this relaxation energy between ions (as seen in ultrasound practices) or an open energy pathway signal between ions when no water molecule is present.

The role of harmonics in nerve function can not be easily dismissed This is evidenced by examination of some correlation of the resonant frequencies of various isotopes of K+ and Rb+. Rb+ very rarely will slip through a K+ ion channel. Table 1 shows the resonant frequencies for different nerve ions:

TABLE 1

| Isotope | Abundance | Spin | Resonant Frequency (MHz) |
| --- | --- | --- | --- |
| K-39 | 93.2582% | 3/2 | 1.9893 |
| K-41 | 6.7302% | 3/2 | 1.0919 |
| Rb-85 | 72.165% | 5/2 | 4.1253 |
| Rb-87 | 27.835% | 3/2 | 13.9807 |
| Na-23 | 100% | 3/2 | 11.2686 |

Harmonics in electromagnetic waves, are defined as multiples of the fundamental frequency or in this case the established resonant frequency. The fundamental or base frequency is considered the first harmonic. Sub-harmonics are fractional multiples of the fundamental resonant frequency. An NQR resonant stimulus ideally is as close to the fundamental frequency as possible. However, the influence of harmonic or sub-harmonic frequencies, both in background science or future applications, should not be ruled out. This can be seen, for example, in the close harmonic relationship between K-39 and Rb-87 and to a somewhat lesser degree in other isotope relationships.

Some limited success of products to enhance nerve function or to relieve pain involve stimulation of the injured or damaged area with vibration introduced by mechanical apparatuses, lasers, or other. Such devices experience limited success by way of inducing a harmonic far away from the fundamental frequency required for true nuclear resonance and are likely to benefit more from thermal properties resulting from electromagnetic or other tissue stimulation rather than targeted nuclear manipulation.

While NQR has proven valuable in such applications as imaging and identification of chemical structures, this technique has never been applied to nerve function. It would, therefore, be advantageous to devise a method of enhancing the nerve ion conduction process to selectively inhibit or amplify nerve ion conduction using nuclear resonance. It would be further desirable if the method could enhance nerve conduction efficiency as well. These and other advantages are achieved in various implementations of the present invention by directly stimulating the atoms transgressing the architecture of the channel utilizing a nuclear quadrupole resonant frequency targeted at the specific ion. By altering the spin state of the atoms, in particular Na+ and K+, they may more readily navigate the natural barriers necessary for the rapid throughput characteristic of ion channels. The method and applications are primarily directed at inadequate nerve function resulting from injury or disease; however, a direct opposite approach is useful in blocking nerve responses for the purpose of pain management. Additionally, viruses and bacteria utilize ion transport mechanisms similar to humans. Further investigation may allow the introduction of blocking mechanisms after additional information is understood concerning the interaction of the sciences and mechanisms involved in ion transport.

With reference now to the figures, and in particular with reference to FIG. 1, there is depicted a therapy environment for nerve ion function enhancement using nuclear resonance stimulation in accordance with one implementation of the present invention. A human has one or more nuclear resonant applicators or stimulators positioned at locations associated with damaged or diseased nerves which are driven by a nerve ion function enhancement apparatus 10, described in further detail below in conjunction with FIG. 2. In this example there is a single applicator 12 attached to the surface of the skin, and two applicators 14a, 14b implanted subcutaneously. Surface applicator 12 is controlled by a wired connection to apparatus 10 and generates a local radio frequency (RF) signal penetrating the skin based on a signal from apparatus 10. The signal may be a control signal, e.g., digitized, which is then decoded by a "smart" version of applicator 12 to determine the appropriate signal parameters (discussed further below), or may be the driving signal itself, i.e., the RF signal with appropriate parameters. Embedded applicator 14a is controlled by a wireless signal from an electromagnetic emitter 15. Again, emitter 15 may send a digitized control signal which is decoded by applicator 14a, or may be the driving signal for a coil or other resonant stimulator within applicator 14a.

The present invention also contemplates an embodiment wherein a first implanted resonant applicator can communicate directly with one or more other implanted resonant applicators to achieve a coordinated function. In the example of FIG. 1, this feature is illustrated by the lightning symbol operatively connecting stimulator 14a to stimulator 14b. This wireless connection may be made using conventional electromagnetic communication, or may be implemented via the human body itself as a communications medium; see, e.g., U.S. Patent Application Publication no. 2008/0046037 (the signals can be acoustic, ultrasonic, or radio frequency).

The stimulating signals are controlled by apparatus 10 in response to direct or indirect feedback from the patient. This feedback can be in the form of electrical nerve measurements or patient response. For the example of FIG. 1, there is a first nerve sensor 16a applied to the surface of the patient's skin with a hard-wired connection to apparatus 10, and a second never sensor 16b implanted subcutaneously with a wireless connection to apparatus 10 via an antenna 18. Implanted sensor 16b can also be in communication with implanted applicator 14b as part of an overall in-body network, i.e., sensor 16b is designed to emit its feedback signal in response to a control or sync signal from applicator 14b. An advanced implementation bridges across an area of an affected nerve to synchronize stimuli with nerve impulses. Sensors 16a, 16b may rely on any conventional measurement techniques for nerve function/activity, such as electromyography (measures how well muscles respond to nerve signals) or nerve conduction study, also called a nerve conduction velocity test (measures how fast and how strong the electrical activity is in a nerve). There could be one or more sensors providing feedback for one RF control signal while the same or other/additional sensors provide feedback for a different RF control signal for an applicator at a different site.

Any of the sensors, as well as any of the input signal devices can be located externally (e.g., on the surface of the skin) or implanted.

FIG. 1 additionally shows a patient sensory feedback device 19. In the simplest implementation this device has a single button or switch which can be depressed/activated by the patient to indicate a specific circumstance, particularly a favorable change such as improved nerve response to a body part or decreased pain. In other embodiments device 19 can have more buttons, e.g., three to indicate (i) a favorable change, (ii) a unfavorable change, or (iii) no change.

Figure 2:
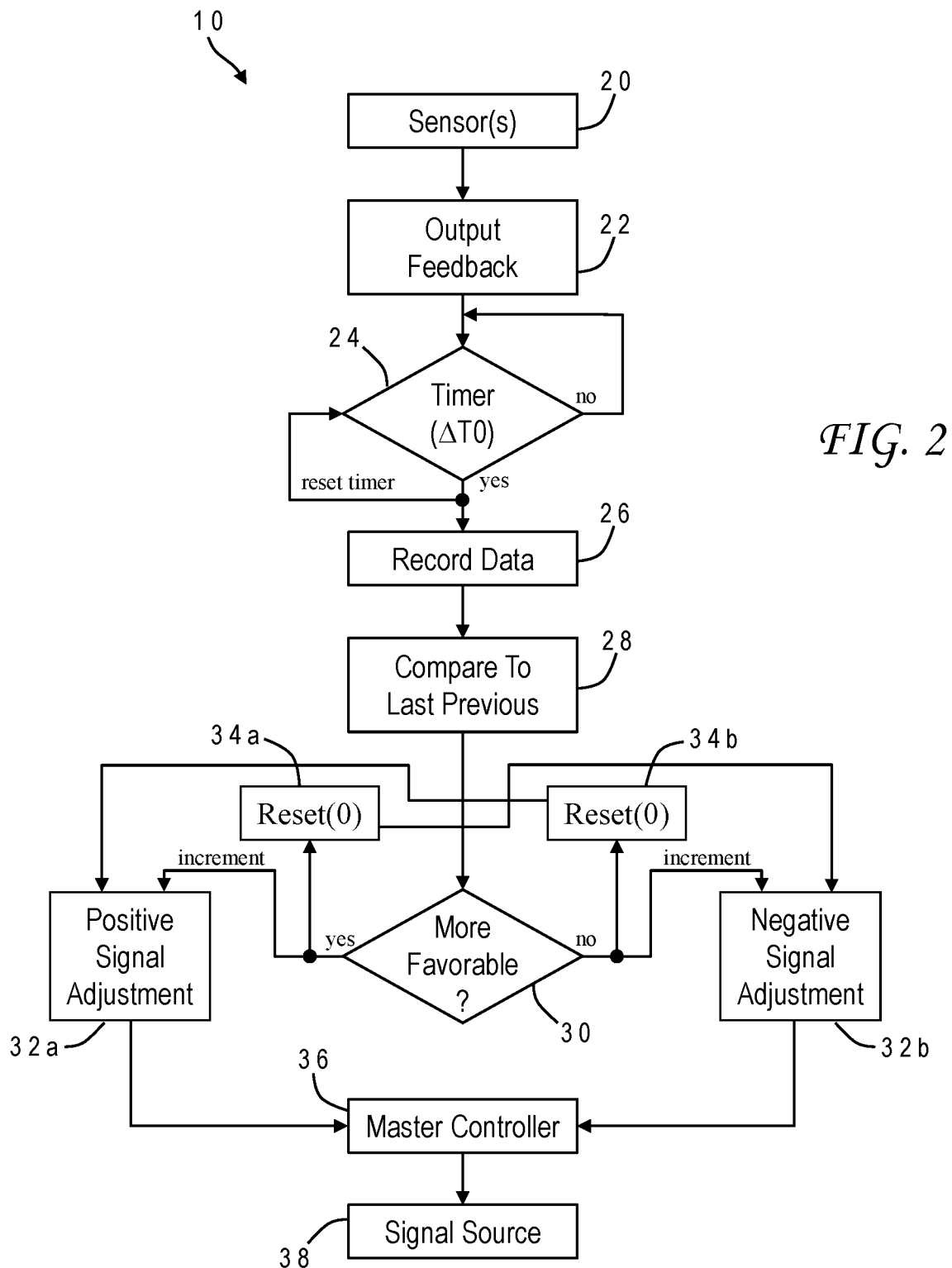
FIG. 2 is a block diagram illustrating feedback logic used by a signal controller in the nerve ion function enhancement apparatus of FIG. 1 to adjust an input signal frequency of a nuclear quadrupole resonance stimulation source in accordance with one implementation of the present invention.

These various feedback signals can then be used by apparatus 10 to tune the output signal which drives/controls the nuclear resonant applicator(s) as seen in FIG. 2.

This feedback logic can be embodied in an electronic circuit such as a programmable logic array. Apparatus 10 receives these sensory input signals and determines the optimum (or near-optimum) operating parameters for NQR nerve stimulation. Corresponding output signals are forwarded to the applicator signal source which then adjusts the performance of the resonant signal accordingly to achieve the required resonant frequency stimulus.

The outputs from sensors 20 are preferably stored in an output feedback buffer 22 but are not necessarily sampled continuously. Buffer 22 can optionally perform other signal conditioning such as averaging. A timer 24 is used to iteratively check buffer 22 until a preset time has passed. This time period ($\Delta T0$) preferably represents the time required for output feedback to stabilize in order to provide more accurate and less variable data, and may vary according to the particular application and feedback source (human versus electronic), e.g., nerve ion conduction amplification versus inhibition. Exemplary time periods may be in the range of 0.1 second to 10 seconds. Once the time has elapsed, the current sensory data are recorded in memory 26, and compared to data from a previous cycle 28. If the current data are more favorable than the previous data 30, an increment is sent to a positive (favorable) signal adjustment circuit 32a, and a reset signal 34a is sent to a negative (unfavorable) signal adjustment circuit 32b. If the current data are not more favorable, an increment is sent to negative signal adjustment circuit 32b, and a reset signal 34b is sent to positive signal adjustment circuit 32a. Positive signal adjustment circuit 32a will upwardly adjust one or more of the signal parameters while negative signal adjustment circuit 32b will downwardly adjust one or more of the signal parameters, as discussed further below in conjunction with FIGS. 3A and 3B. A master controller 36 takes the output of the signal adjustment circuits 32a, 32b and determines optimal signal settings as discussed further below in conjunction with FIG. 4. Those settings are then input to the signal source 38 which drives/controls the resonant applicator(s).

The determination of when data are more favorable depends upon the application. This determination is implicit when the only sensor input is the patient feedback indication. For other sensors, increased muscle response or increased nerve activity/transmission could be used to conclude that the current data are more favorable. Since the sensor input is real-time and ambient based, it inherently compensates for ambient conditions such as temperature and pressure.

Favorability could be characterized in other ways. In this regard, there may be a distinction between optimum results and more favorable (desirable) results. Trade-offs between amplitude and thermal considerations would be one example as mentioned further below. Another would be possible use of sub-harmonic frequencies to achieve partial results while lowering the risk of long-term cell damage. Overall, more favorable data will take into consideration the minimum inputs to achieve the desired results while also minimizing collateral disruptions/damage to normal body functions.

Figure 3A:
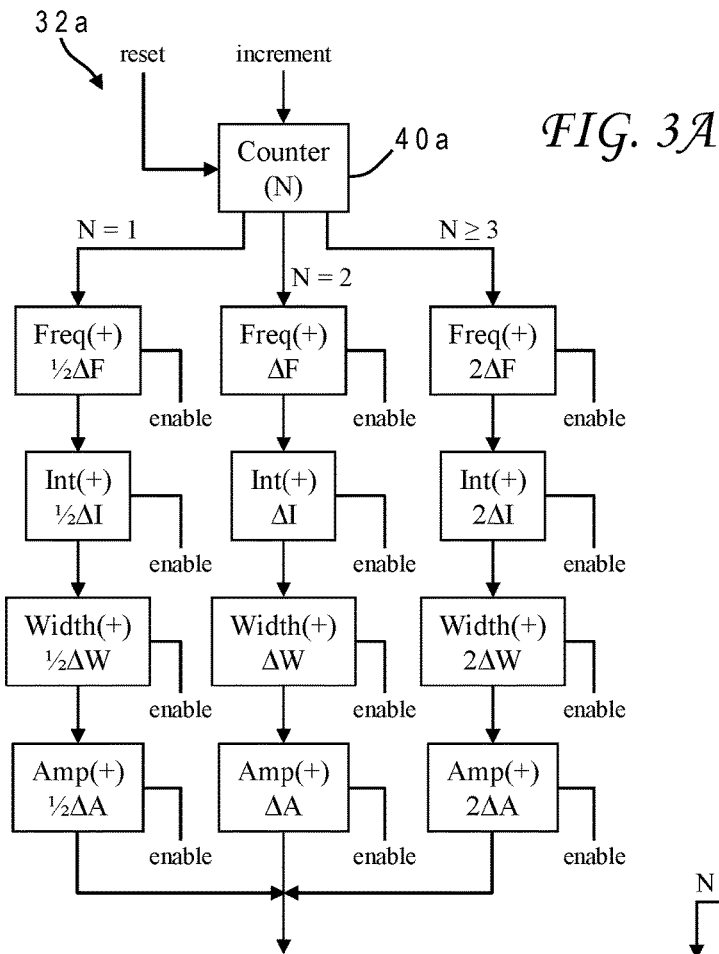
FIGS. 3A and 3B are block diagrams of the positive and negative signal adjustment circuits of FIG. 2 in accordance with one implementation of the present invention.
Figure 3B:
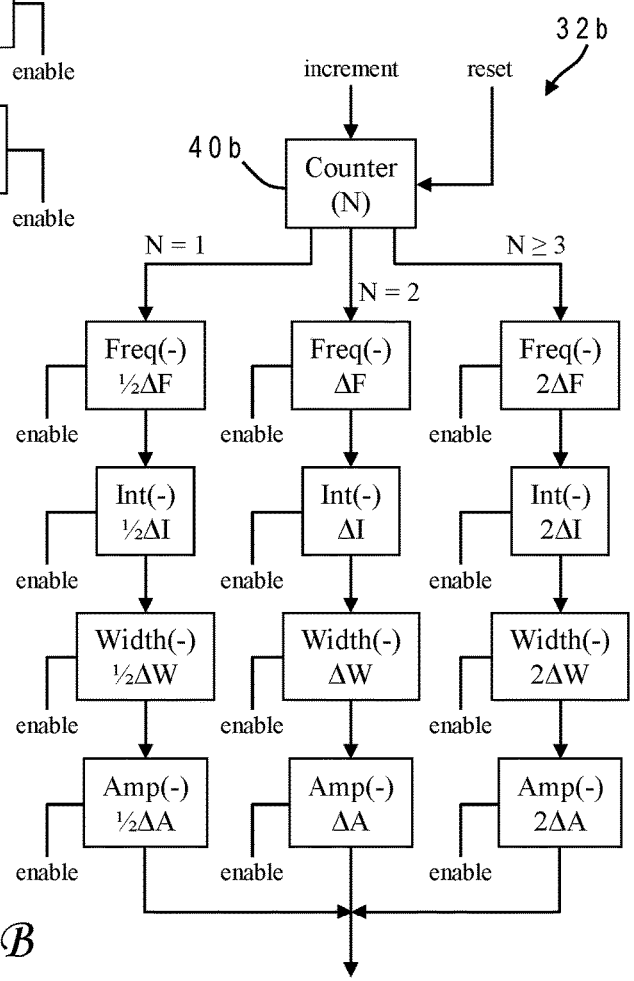

Illustrative embodiments of the signal adjustment circuits are seen in FIGS. 3A and 3B. FIG. 3A shows the positive signal adjustment circuit 32a which includes a counter 40a that receives an increment signal and a reset signal. Counter 40a begins with a zero value and increases by one each time it receives an active increment signal, and returns to zero when the reset signal is active. Thus, the first time there is a favorable comparison for current sensory data, the counter value becomes one. Three different paths are available for the logic depending on the counter value. If the counter value is one, then the magnitudes of the signal parameters are increased by a relatively small amount (compared to the other paths), denoted for this implementation as ½Δ. There is a different predefined delta value for each of four pulsed signal parameters, that is, signal frequency (F), signal interval (I), signal width (W), and signal amplitude (A). Thus, the signal frequency will be increased by ½ΔF for this first logic path, the signal interval will be increased by ½ΔI, the signal width will be increased by ½ΔW, and the signal amplitude will be increased by ½ΔA. Exemplary values for these deltas are discussed further below. If the counter value is two, the signal frequency will be increased by ΔF, the signal interval will be increased by ΔI, the signal width will be increased by ΔW, and the signal amplitude will be increased by ΔA. Similarly, if the counter value is three or more, the signal frequency will be increased by 2ΔF, the signal interval will be increased by 2ΔI, the signal width will be increased by 2ΔW, and the signal amplitude will be increased by 2ΔA. These coefficients for the delta values are exemplary for this implementation, and more or less than three adjustment indications could be provided. A corresponding positive adjustment signal is output from circuit 32a to master controller 36.

For the illustrative implementation negative signal adjustment circuit 32b operates in a similar manner. FIG. 3B shows the negative signal adjustment circuit 32b which includes another counter 40b that receives the other increment signal and the other reset signal. Counter 40b begins with a zero value and increases by one each time it receives an active increment signal, and returns to zero when the reset signal is active. Thus, the first time there is an unfavorable comparison for current sensory data, the counter value becomes one. Three different paths are again available for the logic depending on the counter value. If the counter value is one, then the signal parameters are decreased by ½Δ. Thus, the signal frequency will be decreased by ½ΔF for this first logic path, the signal interval will be decreased by ½ΔI, the signal width will be decreased by ½ΔW, and the signal amplitude will be decreased by ½ΔA. The deltas used for decreasing the parameters are the same as the deltas used for increasing the parameters in this implementation, but different values could be used. If the counter value is two, the signal frequency will be decreased by ΔF, the signal interval will be decreased by ΔI, the signal width will be decreased by ΔW, and the signal amplitude will be decreased by ΔA. Similarly, if the counter value is three or more, the signal frequency will be decreased by 2ΔF, the signal interval will be decreased by 2ΔI, the signal width will be decreased by 2ΔW, and the signal amplitude will be decreased by 2ΔA. A corresponding negative adjustment signal is output from circuit 32b to master controller 36.

Each of these parameter increases/decreases may in some implementations be subject to a respective enable signal (described in conjunction with FIG. 5), i.e., the parameter is increased/decreased only when its corresponding enable signal is active. Alternatively, separate feedback circuits (FIG. 2) can be provided for each parameter.

In this manner, the optimal (or near-optimal) parameters for the resonant stimulation are reached based on real-time feedback.

Figure 4:
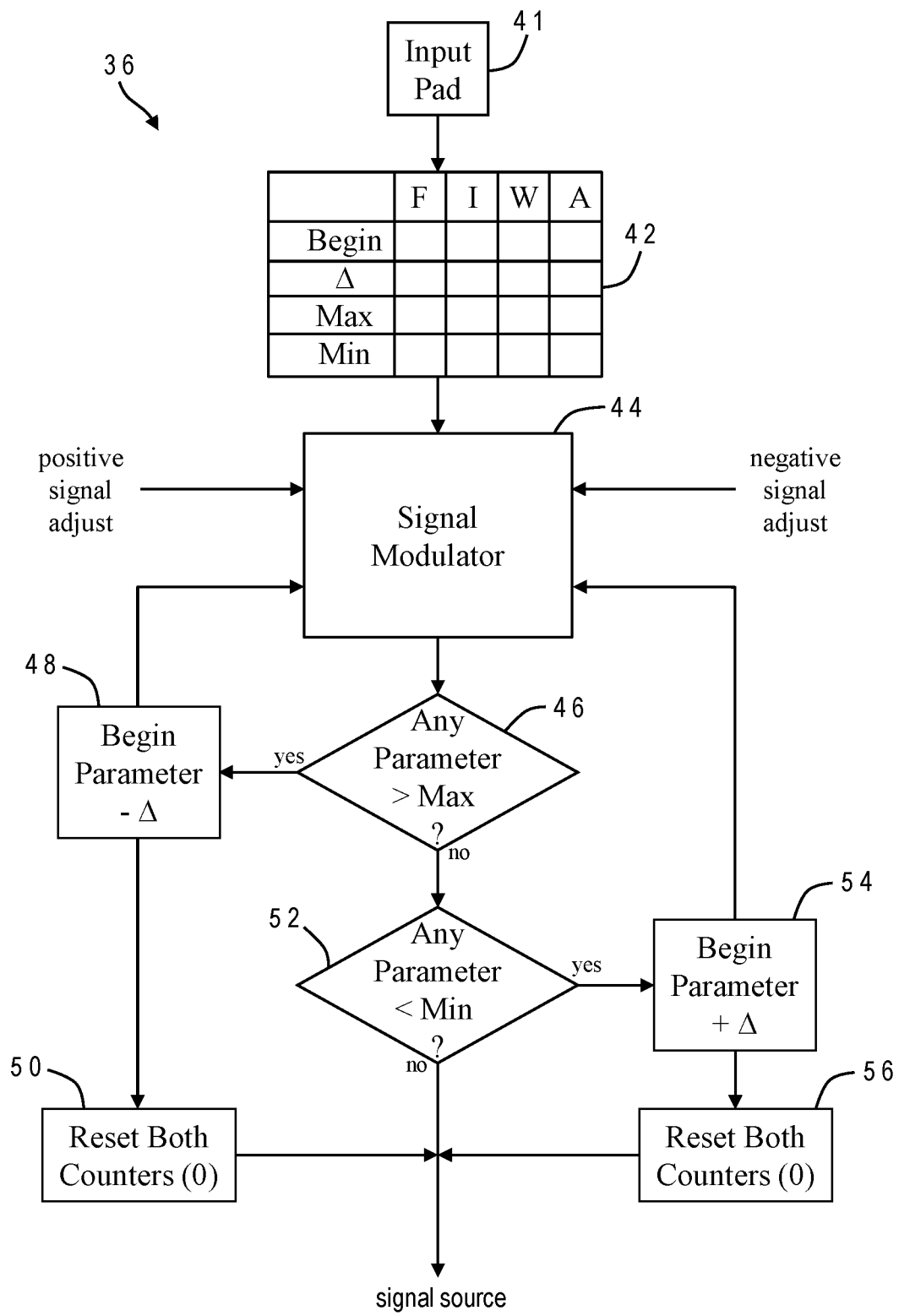
FIG. 4 is a block diagram of the master control unit of FIG. 2 in accordance with one implementation of the present invention.

Master controller 36 uses these adjustment signals to generate the control signal for the signal source 38. As illustrated in FIG. 4, in the preferred implementation master controller 36 has an input pad 41 (or touch-screen, etc.) which allows a user to set default values for variables used in signal generation. Specifically, a non-volatile memory device 42 stores a beginning value ("Begin"), an increment/decrement value ("Δ"), a maximum value ("Max"), and a minimum value ("Min") for each of the four parameters of frequency, interval, width, and amplitude. While the invention contemplates a pulsed resonant stimulation signal, the signal can be applied continuously by setting the beginning interval to zero. Frequency minimum and maximum are ideally manually readjusted periodically to optimize efficiency; the frequencies are generally those corresponding to resonant frequencies for targeted nerve ions, e.g., K+. Exemplary values for the variables are discussed further below.

The default values are fed to a signal modulator 44 which also receives the adjust signals from circuits 32a, 32b, and adjusts the signal parameters in accordance with the adjust signals, i.e., by the indicated amount based on the value of particular delta coefficient. However, if any adjusted parameter ends up being greater than its corresponding maximum 46, then the feedback system resets, by calculating a new beginning parameter 48, and setting signal modulator 44 to use the new beginning parameter. In this implementation, the new beginning parameter is the old beginning parameter decreased by the delta for that parameter when the maximum for the parameter was exceeded. Both of the counters 40a, 40b are reset as well 50. Similarly, if the adjusted parameter ends up being less than the minimum parameter 52, then the feedback system again resets, by calculating a new beginning parameter 54, and setting signal modulator 44 to use the new beginning parameter. In this implementation, the new beginning parameter is the old beginning parameter increased by the delta for that parameter when the minimum for the parameter was exceeded. If all parameters of the adjusted signal from signal modulator 44 are within the respective max/min limits (both no branches for decision boxes 46, 52), they are then fed to the signal source.

The logic for master controller 36 could examine the parameters for min/max comparison in a specific order such that one base parameter would take precedence even if other parameters had also exceeded the min/max. For example, the begin signal frequency could be reset without immediately adjusting the other three begin parameters. Additionally, the master controller could utilize appropriate logic to consider different combinations of the parameter values; for example, a signal might have become adjusted to the point that all four of the signal parameters are close to (but not exceeding) their respective maximums. This scenario might still be a trigger for signal reset if the combined effect of all of the parameters (as a mathematical formula) is to exceed some predetermined overall power threshold deemed as being too dangerous.

Figure 5:
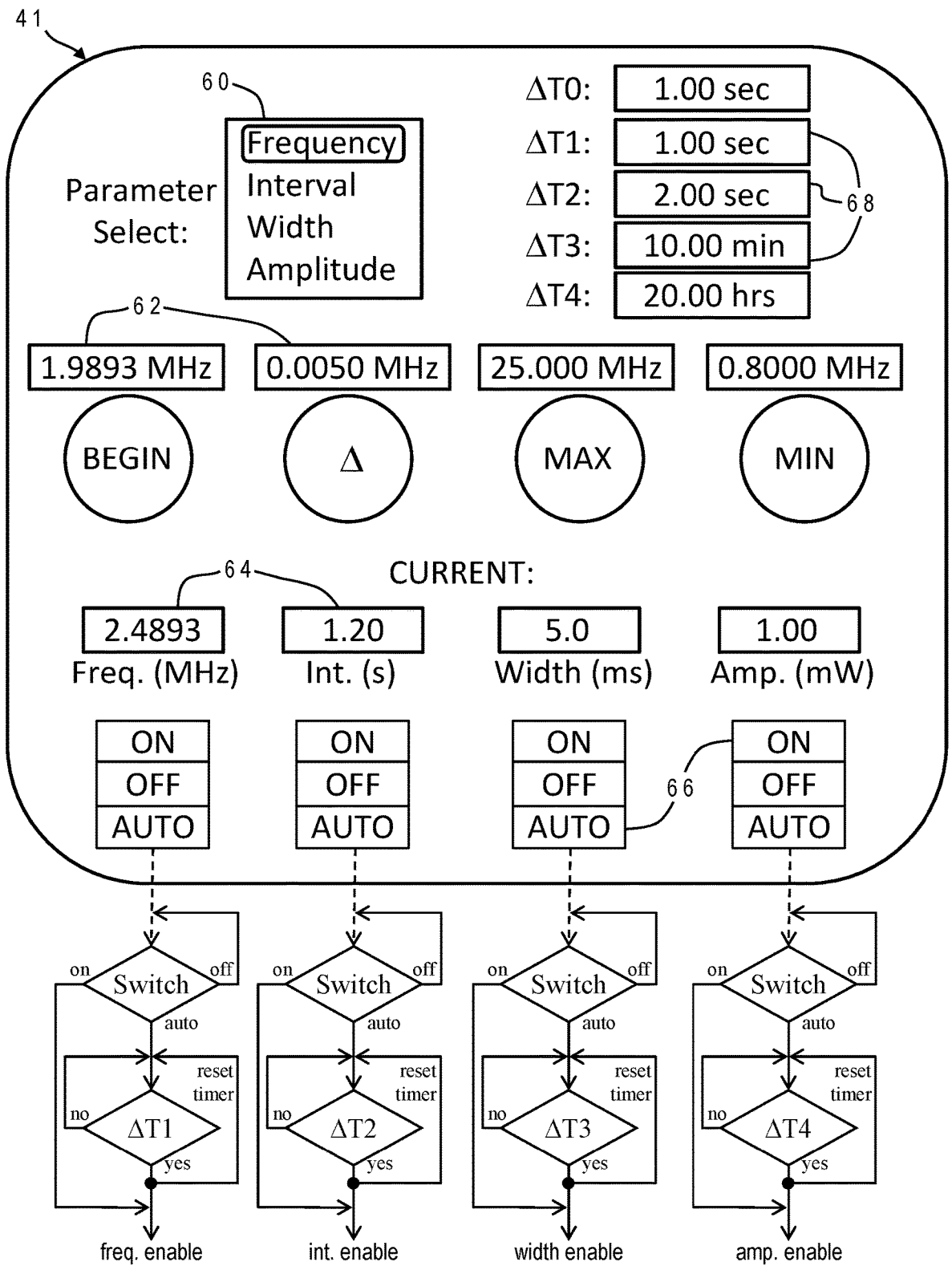
FIG. 5 is a plan view of an input pad for the master control unit with selection logic for different signal parameters in accordance with one implementation of the present invention.

FIG. 5 illustrates one user interface that can be provided by input pad 41 and used with master controller 36. The user interface includes one or more display fields (e.g., LCD or LED) and one or more buttons or knobs for inputting the various programmable values. All of these features may be embodied virtually with a touch screen rather than physical hardware. In this example, there is a "Parameter Select:" window which allows the user to select which of the four signal parameters are to be set. As pictured, the "Frequency" parameter has been selected as indicated by the box around that term or other highlighting. There are also four fields 62 representing, for a given parameter, its beginning value, its delta, its maximum, and its minimum. Thus, with the "Frequency" parameter selected, these fields allow the user to set the starting frequency, the frequency delta, the maximum frequency, and the minimum frequency. Other begin, delta, max and min parameters are set by selecting the appropriate parameter in window 60.

The current signal parameters (reflecting any adjustments from the feedback circuits) are shown for convenience in four other fields 64. These fields are for display only. This information can help an operator to manually adjust certain parameters and/or enable their automatic adjustment. Four switches 66 are provided, one under each field 64, which allow independent control for adjustment of each of the four parameters. Each switch has three settings, "ON", "OFF" and "AUTO". As shown by the decision logic below each switch in FIG. 5, selecting the "OFF" setting for a parameter means that parameter will not be adjusted, selecting the "ON" setting for a parameter means it will be continuously adjusted with each compare cycle of timer 24 (FIG. 2), and selecting the "AUTO" setting for a parameter means it will be adjusted at a custom rate. This embodiment allows for separate timer settings for each of the four parameters, i.e., time $\Delta T1$ for signal frequency, time $\Delta T2$ for signal interval, time $\Delta T3$ for signal width, and time $\Delta T4$ for signal amplitude. The user interface on input pad 41 can also show the time values T0-T4 in modifiable fields 68. Setting any of these $\Delta T1$-$\Delta T4$ to zero will result in continuous adjustment, i.e., as if the "ON" setting had been selected for that timer. These timers can be implemented by having the switches control the respective enable lines seen in FIGS. 3A-3B, e.g., an active signal from the frequency switch will enable all of the frequency adjustments in circuit 32a (+½$\Delta F$, +$\Delta F$, +2$\Delta F$) as well as the frequency adjustments in circuit 32b (−½$\Delta F$, −$\Delta F$, −2$\Delta F$).

For example, it may be desirable to run the frequency loop continuously or at a relatively fast rate (once every minute), while interval and width may have to be run every day, week, month, once during set up, or only in a controlled setting in a doctor's office. The primary purpose of the amplitude parameter is to prevent tissue damage by exceeding the maximum power recommended. The second purpose is to determine a power setting less than the maximum (if possible) that achieves a partial desired result. In other words, the "more favorable" data found by increasing the amplitude may not be linear. Therefore, a tradeoff may be desired when 80% of the desired result is achieved by using 50% of the maximum amplitude. It may also be beneficial to run independent parameters depending upon the application. For example, it might turn out to be important to vary time duration of interval logic for a Parkinson's patient, or amplitude logic in a multiple sclerosis patient, or width logic in a bridged sensor upstream on the same nerve.

Given all of the different possible outcomes and goals for the potential applications, the specific values of the parameter variables can vary considerably. The following values in Table 2 are accordingly deemed exemplary as directed to K+ ions but not restrictive as other values may be useful for K+ as well as other ions:

TABLE 2

| Parameter | Begin | Δ | Max | Min |
|---|---|---|---|---|
| Frequency | 1.9893 MHz | 0.0050 MHz | 25.000 MHz | 0.8000 MHz |
| Interval | 1.0 sec | 0.01 sec | 100 sec | 0.1 sec |
| Width | 5.0 msec | 0.01 msec | 500 ms | 0.1 ms |
| Amplitude | 1.0 mW | 0.01 mW | 100 mW | 0.1 mW |

Specific defaults are not critical since all parameters will eventually be determined by trial-and-error and can be reprogrammed as desired.

While the foregoing disclosure describes a single signal output for nuclear resonance stimulation source 38, more than one ion can be simultaneously targeted by utilizing more than one stimulus frequency. Such an implementation can utilize two or more stimulation sources with two or more corresponding feedback systems. Alternatively, a single stimulation source may be used which is driven by a composite signal having dual frequency components. The user interface of input pad 41 can be appropriately altered to allow selection/setting of a second set of signal parameters for the second stimulation source. Referring back to FIG. 1, stimulator 12 could operate with the first set of signal parameters, while stimulator 14a could operate with the second set of signal parameters. In some applications it is possible that a signal source may overlap tissue from an adjacent signal source using different input parameters. It is not anticipated that different parameter inputs from a first source, with a particular frequency, will cause interference with a second source.

The present invention thereby achieves superior control in a feedback system for enhancing nerve ion conduction using nuclear resonance stimulation. The individual adjustment of signal parameters allows customization of applications while limiting unintended collateral damage to surrounding tissue. Nerve ion channels have been proven to be very adaptive of their environment so it is entirely possible that a damaged or diseased channel may relearn how to function normally again after returning to its natural structure through the process of the present invention.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. For example, the invention has been described with reference to a resonant stimulator using a radio frequency signal, but other means may be used such as mechanical vibration, lasers, etc., provided they are targeted for nuclear resonant stimulation of nerve ions. It is therefore contemplated that such modifications can be made without departing from the spirit or scope of the present invention as defined in the appended claims.

What is claimed is:

1. A method of enhancing nerve function in a human comprising:
   stimulating at least one selected nerve ions including a potassium ion using nuclear resonance to alter ion channel conductivity of the at least one selected nerve ions, the nuclear resonance stimulation having one or more signal parameters including a frequency targeted for the at least one selected nerve ion;
   iteratively sensing one or more indicia of nerve function; and
   automatically adjusting one or more signal parameters of the nuclear resonance stimulation in real-time based on the sensed indicia.

2. The method of claim 1 wherein:
   the one or more signal parameters further include an interval, a width, and an amplitude; and
   said adjusting allows independent adjustment of each of the one or more signal parameters.

3. The method of claim 1 wherein said adjusting selectively increases or decreases the frequency of the nuclear resonance stimulation by a predefined frequency adjustment value.

4. The method of claim 1 wherein said stimulating utilizes nuclear quadrupole resonance.

5. The method of claim 4 wherein said stimulating emits an electromagnetic signal having a frequency which targets a nuclear resonance frequency of the potassium ion.

6. The method of claim 1 wherein the nuclear resonance stimulation includes harmonic and sub-harmonic nuclear resonant frequencies.

7. The method of claim 1 wherein:
   said one or more indicia indicates an improvement in nerve function; and
   said adjusting responsively selectively increases or decreases a magnitude of the one or more signal parameters.

8. The method of claim 1 wherein:
   the at least one selected nerve ions include a first ion isotope and a second ion isotope;
   the nuclear resonance stimulation frequency is a first frequency targeted for the first ion isotope; and
   said stimulating further simultaneously uses nuclear resonance stimulation having a second frequency targeted for the second ion isotope.

9. An apparatus for enhancing nerve function comprising:
   one or more nuclear resonance stimulation sources which stimulate at least one selected nerve ions including a potassium ion using nuclear resonance to alter ion channel conductivity of the at least one selected nerve ions, the nuclear resonance stimulation having one or more signal parameters including a frequency targeted for the at least one selected nerve ion;
   at least one sensor which iteratively senses one or more indicia of nerve function; and
   a control unit which automatically adjusts one or more signal parameters of said one or more nuclear resonance stimulation sources in real-time based on the sensed indicia.

10. The apparatus of claim 9 wherein:
    the one or more signal parameters further include an interval, a width, and an amplitude; and
    said control unit allows independent adjustment of each of the one or more signal parameters.

11. The apparatus of claim 9 wherein said control unit selectively increases or decreases the frequency of the nuclear resonance stimulation by a predefined frequency adjustment value.

12. The apparatus of claim 9 wherein at least one of said one or more nuclear resonance stimulation source utilizes nuclear quadrupole resonance.

13. The apparatus of claim 12 wherein at least one of said one or more nuclear resonance stimulation sources emits an electromagnetic signal having a frequency which targets a nuclear resonance frequency of the potassium ion.

14. The apparatus of claim 9 wherein the nuclear resonance stimulation includes harmonic and sub-harmonic nuclear resonant frequencies.

15. The apparatus of claim 9 wherein:
    said one or more indicia indicates an improvement in nerve function; and
    said control unit responsively selectively increases or decreases a magnitude of the one or more signal parameters.

16. The apparatus of claim 9 wherein the at least one selected nerve ions include a first ion isotope and a second ion isotope;
    the nuclear resonance stimulation frequency is a first frequency targeted for the first ion isotope; and
    said one or more nuclear resonance stimulation sources further simultaneously stimulates the second ion isotope using a second frequency targeted for the second ion isotope.

17. A feedback control unit for a nuclear resonance stimulation source which enhances nerve ion function comprising:
    one or more inputs for iteratively receiving sensory data relating to nerve function;
    control logic which examines the sensory data to automatically determine an operational adjustment factor for at least one signal parameter of the nuclear resonance stimulation source targeted for at least one selected nerve ions including a potassium ion; and
    an output which provides a real-time signal indicative of the operational adjustment factor.

18. The feedback control unit of claim 17 further comprising a user interface which allows the at least one signal parameter to be programmably set.

19. The feedback control unit of claim 18 wherein said user interface further allows a signal parameter adjustment value to be programmably set.

20. The feedback control unit of claim 17 wherein said control logic adjusts the at least one signal parameter based on a comparison of current sensory data to previously-recorded sensory data.

21. The feedback control unit of claim 17 wherein the at least one signal parameter is a frequency targeted for nuclear resonance stimulation of the at least one selected nerve ion.

22. The feedback control unit of claim 21 wherein the nuclear resonance stimulation includes harmonic and subharmonic nuclear resonant frequencies.

23. The feedback control unit of claim 17 wherein:
the at least one signal parameter includes a frequency, an interval, a width, and an amplitude;
and said control logic independently determines respective operational adjustment factors for each of the at least one signal parameter.

\* \* \* \* \*